(12) United States Patent
Davanzo

(10) Patent No.: US 10,350,323 B2
(45) Date of Patent: Jul. 16, 2019

(54) EMANATOR DEVICE

(71) Applicant: RECKITT BENCKISER FINISH B.V., Hoofddorp (NL)

(72) Inventor: Mauro Davanzo, Ludwigshafen (DE)

(73) Assignee: RECKITT BENCKISER FINISH B.V., Hoofddorp (NL)

( * ) Notice: Subject to any disclaimer, the term of this patent is extended or adjusted under 35 U.S.C. 154(b) by 162 days.

(21) Appl. No.: 15/152,928

(22) Filed: May 12, 2016

(65) Prior Publication Data

US 2016/0256587 A1    Sep. 8, 2016

Related U.S. Application Data

(63) Continuation of application No. 14/000,874, filed as application No. PCT/GB2012/050296 on Feb. 10, 2012, now Pat. No. 9,339,577.

(30) Foreign Application Priority Data

Feb. 25, 2011    (GB) .................................. 1103251.3

(51) Int. Cl.
*A61L 9/12*        (2006.01)
*A61L 2/18*        (2006.01)
(Continued)

(52) U.S. Cl.
CPC ..................... *A61L 9/12* (2013.01); *A61L 2/18* (2013.01); *A61L 2/23* (2013.01); *A61L 9/05* (2013.01);
(Continued)

(58) Field of Classification Search
CPC ..... A61L 9/12; A61L 2/18; A61L 2/23; A61L 9/05
See application file for complete search history.

(56) References Cited

U.S. PATENT DOCUMENTS

2004/0199985 A1    10/2004   Wilson
2008/0011870 A1    1/2008    Link et al.

FOREIGN PATENT DOCUMENTS

CN    101384283 A    3/2009
EP    2030638 A1    3/2009
(Continued)

OTHER PUBLICATIONS

International Search Report and Written Opinion dated Apr. 25, 2012 for priority application PCT/GB2012/050296.
(Continued)

*Primary Examiner* — Sean E Conley
(74) *Attorney, Agent, or Firm* — Troutman Sanders LLP; Ryan Schneider; Chris Davis

(57) ABSTRACT

An emanator device for emanating an air treatment agent into the surrounding air comprises a housing which contains a solid or liquid source of the air treatment agent, wherein the housing comprises a blister or capsule containing an air treatment agent and a plurality of openings which are sufficiently small that they can be closed by a film or plug of water. For example the openings may be provided by a gauze or mesh. The openings do not inhibit the emanation of air treatment agent released from the blister, but when the emanator device is subject to wet conditions, as may happen in a dishwashing machine, the openings are blocked by a film or plug of water. The air treatment agent does not therefore enter the water, where it may have caused adverse effects, or simply have been wasted. Under dry conditions, however, emanation occurs normally.

8 Claims, 4 Drawing Sheets

(51) Int. Cl.
*A61L 2/23* (2006.01)
*A61L 9/05* (2006.01)
*E03D 9/00* (2006.01)

(52) U.S. Cl.
CPC ........ *E03D 9/007* (2013.01); *A61L 2202/121* (2013.01); *A61L 2202/17* (2013.01); *A61L 2209/131* (2013.01)

(56) References Cited

FOREIGN PATENT DOCUMENTS

| | | |
|---|---|---|
| EP | 2133477 A1 | 12/2009 |
| RU | 2492296 C2 | 8/2008 |
| WO | 2004069982 A1 | 8/2004 |
| WO | 2005102141 A1 | 11/2005 |
| WO | 2008141473 A1 | 11/2008 |
| WO | 2009086947 A1 | 7/2009 |

OTHER PUBLICATIONS

Combined Search and Examination Report Under SEctions 17 and 18(3) dated Jun. 23, 2011 for priority British patent application GB1103251.3.
Dthce Action in related Cn Application No_ CN201280010146.3, mailed Dec. 18, 2014.

EMANATOR DEVICE

CROSS-REFERENCE TO RELATED APPLICATIONS

This application is a continuation of U.S. Ser. No. 14/000,874, filed 5 Dec. 2013, now U.S. Pat. No. 9,339,577, which is a US National Stage entry of International Application No. PCT/GB2012/050296, filed 10 Feb. 2012, which claims the benefit of GB 1103251.3, filed 25 Feb. 2011, all of which are herein fully incorporated by reference.

BACKGROUND OF THE INVENTION

This invention relates to an emanator device for delivering an air treatment agent into the surrounding air.

The invention relates in particular to an emanator device for delivering an air treatment agent into the surrounding air, for use in an environment which is alternately wet and dry.

WO 2004/069982 A1 describes an emanator for emanating one or more active component(s), which preferably comprises a surfactant and fragrance. Typically the emanator is for use in a dishwashing machine. The emanator comprises a blister which contains the active component(s) as a concentrated liquid, within a permeable polymeric membrane, through which the active component(s) gradually diffuses. The blister is retained in a cage-like retaining structure. The arrangement, in such a device, is such that the blister is washed over by water in "wet phases" of the dishwashing cycle; and at other times is dispensed into the ambient air. Thus, emanation of the active component(s) occurs without interruption, whether into the ambient air or into the ambient water.

WO 2005/102141 A1 describes an emanator of a similar type, having an aperture or apertures whose size may be varied, in order to provide different rates of release of the active component(s). As in the device of WO 2004/069982 A1, the emanation of the active component(s) is into the ambient environment, whether into water or into air, and thus proceeds without interruption.

It is desirable to fragrance the air in a dishwashing device, to mask the chemical smell sometimes found in a dishwasher, and the odour of dirty dishes and cutlery waiting to be washed. However it is undesirable to add fragrance to the water in the wash cycle, because the crockery and cutlery may have a taint which some users can detect.

WO 2008/141473 A1 describes a malodour-counteracting device for use in an automatic dishwashing machine. The device addresses a problem, that there is increased evaporation of fragrance during the wash cycle, followed by reduced evaporation between washes. The latter time is often when more, rather than less, fragrance is needed, given that dirty dishes and cutlery are loaded into the dishwashing machine, and may be kept there for some hours, before the dishwashing machine is operated. To solve this problem a device is described having a downwardly-open body holding a gradually-releasable fragrance source, and a larger, upwardly open, dish. The body and the dish overlap, but are not sealed to one another; fragranced air can leave the device though a space between the dish and the body. However, during the wet phase of a dishwasher cycle water collects in the dish and thereby rises over the space, preventing fragranced air from leaving the device. However the fragrance source is not itself immersed in water. Fragranced air can not escape from the device until the level of water in the dish falls, by evaporation, to open the space.

The device of WO 2008/141473 A1 achieves the objective of preventing fragrance release during the wet phase, by use of a collected water barrier. However, the device described is aesthetically unappealing, and has functional limitations. The "dish" of the device needs to retain a substantial volume of water in order for the water to close the passage through which fragrance could otherwise escape. To open the passage to its maximum degree appears to require the complete absence of water in the dish. Moreover it is sometimes found that water collected in upwardly-open formations, such as the bases of cups, can contain residues of dirty water, in certain makes of dishwashing machine. This can be expected to occur on occasion, in the upwardly open "dish" of the device of WO 2008/141473 A1. Providing a device which relies upon an upwardly-open dish for alternating closure and non-closure of an emission port or ports is not an optimal technical solution.

BRIEF SUMMARY OF THE INVENTION

It is an object of the present invention to provide an emanator device for delivering an air treatment agent effectively into the air, during dry phases of operation whilst inhibiting (and preferably preventing) release of the air treatment agent into water, during wet phases of operation.

In one embodiment of the present invention, the invention provides an emanator device for emanating an air treatment agent into the surrounding air, the emanator device comprising a housing which contains a source of an air treatment agent, wherein the housing comprises a wall and a plurality of openings, wherein the openings are the only openings available for passage into the surrounding air of the air treatment agent emanated by the source thereof, and wherein each of the openings is sufficiently small that it can be closed by a film or plug of water.

In some embodiments, the area of each opening of the emanator device does not exceed 4 $mm^2$. In other embodiments, the area of each opening does not exceed 2 $mm^2$. In still other embodiments, the area of each opening does not exceed 1 $mm^2$. In still other embodiments, the area of each opening does not exceed 0.5 $mm^2$. In yet other embodiments, the area of each opening does not exceed 0.1 $mm^2$.

In some embodiments, the total area of the openings of the emanator device is not less than 50 $mm^2$. In other embodiments, the total area of the openings of the emanator device is not less than 100 $mm^2$.

In some embodiments, the openings of the emanator device are arranged as an array or group.

In some embodiments, the openings of the emanator device are provided as a gauze. In certain aspects of these embodiments, the gauze may be mounted in a window in the wall of the housing, and represents the only exit route from the device for the treated air.

In some embodiments, the air treatment agent comprises an agent selected from the group consisting of a fragrance, an airborne sanitizing agent, and an airborne malodor absorber.

In another embodiment of the present invention, the invention provides an air treatment method for a household apparatus which has dry phases of operation and wet phases of operation, the method comprising providing the emanator device as described herein and emanating the air treatment agent during the dry phases of the household apparatus, but not during the wet phases, wherein each of the openings is sufficiently small, that selectively during a wet phase it is closed by the film or plug of water.

In some embodiments of the above method, the wet phase is a washing or flushing phase.

In some embodiments of the above method, the household apparatus is selected from the group consisting of a laundry washing machine, a dishwashing machine, and a lavatory.

In some embodiments of the above method, during the wet phases, the emanator device is subjected to water in a non-immersive manner.

BRIEF DESCRIPTION OF THE DRAWINGS

The accompanying Figures, which are incorporated in and constitute a part of this specification, illustrate several aspects described below.

DESCRIPTION OF THE INVENTION

Figure 1:
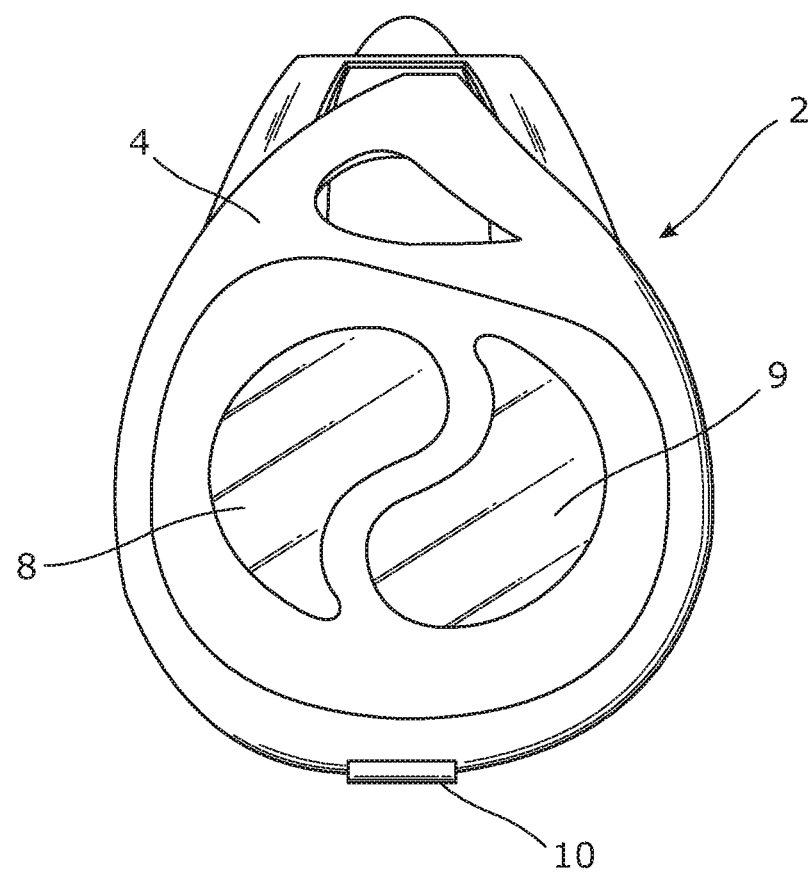
FIG. 1 shows a first embodiment of emanator device in front elevation.

To facilitate an understanding of the principles and features of the various embodiments of the invention, various illustrative embodiments are explained below. Although exemplary embodiments of the invention are explained in detail, it is to be understood that other embodiments are contemplated. Accordingly, it is not intended that the invention is limited in its scope to the details of construction and arrangement of components set forth in the following description or examples. The invention is capable of other embodiments and of being practiced or carried out in various ways. Also, in describing the exemplary embodiments, specific terminology will be resorted to for the sake of clarity.

It must also be noted that, as used in the specification and the appended claims, the singular forms "a," "an" and "the" include plural references unless the context clearly dictates otherwise. For example, reference to a component is intended also to include composition of a plurality of components. References to a composition containing "a" constituent is intended to include other constituents in addition to the one named. In other words, the terms "a," "an," and "the" do not denote a limitation of quantity, but rather denote the presence of "at least one" of the referenced item.

Also, in describing the exemplary embodiments, terminology will be resorted to for the sake of clarity. It is intended that each term contemplates its broadest meaning as understood by those skilled in the art and includes all technical equivalents which operate in a similar manner to accomplish a similar purpose.

Ranges may be expressed herein as from "about" or "approximately" or "substantially" one particular value and/or to "about" or "approximately" or "substantially" another particular value. When such a range is expressed, other exemplary embodiments include from the one particular value and/or to the other particular value. Further, the term "about" means within an acceptable error range for the particular value as determined by one of ordinary skill in the art, which will depend in part on how the value is measured or determined, i.e., the limitations of the measurement system. For example, "about" can mean within an acceptable standard deviation, per the practice in the art. Alternatively, "about" can mean a range of up to ±20%, preferably up to ±10%, more preferably up to ±5%, and more preferably still up to ±1% of a given value. Alternatively, particularly with respect to biological systems or processes, the term can mean within an order of magnitude, preferably within 2-fold, of a value. Where particular values are described in the application and claims, unless otherwise stated, the term "about" is implicit and in this context means within an acceptable error range for the particular value.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

Throughout this description, various components may be identified having specific values or parameters, however, these items are provided as exemplary embodiments. Indeed, the exemplary embodiments do not limit the various aspects and concepts of the present invention as many comparable parameters, sizes, ranges, and/or values may be implemented. The terms "first," "second," and the like, "primary," "secondary," and the like, do not denote any order, quantity, or importance, but rather are used to distinguish one element from another.

It is noted that terms like "specifically," "preferably," "typically," "generally," and "often" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention. It is also noted that terms like "substantially" and "about" are utilized herein to represent the inherent degree of uncertainty that may be attributed to any quantitative comparison, value, measurement, or other representation.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "50 mm" is intended to mean "about 50 mm."

It is also to be understood that the mention of one or more method steps does not preclude the presence of additional method steps or intervening method steps between those steps expressly identified. Similarly, it is also to be understood that the mention of one or more components in a composition does not preclude the presence of additional components than those expressly identified.

The materials described hereinafter as making up the various elements of the present invention are intended to be illustrative and not restrictive. Many suitable materials that would perform the same or a similar function as the materials described herein are intended to be embraced within the scope of the invention. Such other materials not described herein can include, but are not limited to, materials that are developed after the time of the development of the invention, for example. Any dimensions listed in the various drawings are for illustrative purposes only and are not intended to be limiting. Other dimensions and proportions are contemplated and intended to be included within the scope of the invention.

It is an object of the present invention to provide an emanator device for delivering an air treatment agent effectively into the air, during dry phases of operation whilst inhibiting (and preferably preventing) release of the air treatment agent into water, during wet phases of operation.

In accordance with a first aspect of the present invention there is provided an emanator device for emanating an air treatment agent into the surrounding air, the emanator device comprising a housing which contains a solid or liquid source of the air treatment agent, wherein the housing comprises a wall and a plurality of openings, wherein the openings are the only openings available for passage into the surrounding air of the air treatment agent emanated by the source thereof, characterized in that each of the openings is sufficiently small that it can be closed by a film or plug of water.

Such an emanator device can in principle be used with benefit in any environment in which there is a "dry" phase, and a "wet" phase. A wet phase may typically be a washing or flushing phase. Such an emanator device may be used, for example, in a laundry washing machine, in a dishwashing machine, or as a lavatory ITB ("in-the-bowl") device.

The air treatment agent may, for example, comprise a fragrance, or an airborne sanitizing agent, or an airborne malodour absorber. Preferably it comprises a fragrance.

In the present invention the closing of the openings is achieved by a film or plug of water. This is all that is needed. In contrast, in the prior art device of WO 2008/141473 A1 closure is achieved by a mass of water, as a bulk component filling the space. It will be appreciated that the mass of water in the films or plugs which close the openings is very small in comparison. This small mass means that the device of the present invention can be extremely sensitive: the closure of the openings by films or plugs of water can occur very quickly, after the beginning of a wet phase of operation; conversely, evaporation can be expected to take place quickly after the commencement of a dry phase, thereby re-commencing the emanation of the air treatment agent into the air.

In embodiments of the invention a plurality of openings, and preferably all of the openings, are closed by a common film of water.

In embodiments of the invention each opening may be closed by a film of water, and the films are separate from each other.

In embodiments of the invention each of the openings is closed by a plug of water. The plugs may be drawn into the openings by capillary action.

In embodiments of the invention each of the openings is closed by a plug and by a film (separate films, or one or more common film(s)).

Common to each embodiment is the fact that the openings may be blocked by water.

Each of the openings is suitably of size such that it can be closed by water at an operating temperature. This may be room temperature, for example 20° C., or it may be an elevated temperature, as employed in a laundry washing machine or a dishwashing machine.

In the case of a laundry machine the temperature of operation may be from 20° C-80° C. and the size of the openings is such that they can be closed by water at all temperatures in the range from 20° C-80° C.

In the case of a dishwashing machine the temperature of operation may be from 20° C.-80° C. and the size of the openings is such that they can be closed by water at all temperatures in the range from 20° C-80° C.

In the case of a lavatory the flushing water may be from 5° C. (e.g. when drawn immediately from an external supply) to room temperature, for example 20° C-30° C., or higher. The size of the openings is such that they can be closed by water at all temperatures in the range from 5° C-40° C.

In practice it is believed that when the area of each opening is not greater that 4 $mm^2$, good operation can be achieved. Preferably the area of each opening does not exceed 2 $mm^2$, and preferably does not exceed 1 $mm^2$, and more preferably does not exceed 0.5 $mm^2$. Most preferably the area of each opening does not exceed 0.1 $mm^2$.

Preferably the openings are arranged as an array or group. When the openings are closed by films, these may in practice be provided by a single overall film.

The openings may be provided as through-holes, for example pinholes, provided through the wall of the housing. Water may plug through-holes, being drawn into them by capillary action. Alternatively the openings may be provided as a grid or mesh or gauze. Such a grid or mesh or gauze may be mounted in a window in the wall of the housing, and may then represent the only exit from the device, for the treated air.

The grid or mesh may be of metal or polymeric material. Stainless steel is a preferred material.

The skilled person will understand that the maximum size of the openings that can be selected will depend on surface tension factors, and that that depends in turn on the material chosen.

Preferably the total area of the openings is not less than 50 $mm^2$, preferably not less than 100 $mm^2$.

Alternatively the openings may be narrow spacings in a grating. Provided the spacings are sufficiently small that water may close the spacings this is within the scope of the present invention.

Alternatively the openings are the openings in a textile sheet product, for example a scrim or non-woven sheet product, made of a material which is impermeable to the air treatment agent. A suitable material does not provide a diffusion route by which the air treatment agent can leave the housing.

The emanator device may be of a generally flat or discoid form, having front and rear panels, which contact each other at their respective peripheries, or which are spaced apart by a wall in the form of a narrow band.

Preferably the openings are provided in one of the panels only; and preferably in the panel which is intended to be the rear panel at the point of sale and/or in use.

Preferably the front and rear panels may be separated from each other to replace the source of the air treatment agent, and then brought together again, to close the emanator device, containing the new source of the air treatment agent. Preferably they seal to each other so that the openings are the only escape route for fragranced air, from the device. They may snap together. They may, or may not, require a seal, depending on the design.

However the front and rear panels are not necessarily separable. They may suitably be connected by a hinge. When the panels are of a thermoplastics material the front and rear panels and the hinge may be moulded as one part; the hinge is suitably a plastics web.

When front and rear panels are provided, to be separated and brought together when required, the source of the air treatment agent may be in one panel, and the gauze in the other, such that when the panels come together the openings are caused to overlie the source of the air treatment agent, and provide the only escape for the air treatment agent.

The device may have a hook, for mounting purposes. Preferably the hook projects over part of the rear panel of the emanator device.

Alternatively the device need not have a hook, but could have alternative securement means, or no securement means. It could stand, for example. In a dishwashing machine, for example, it could stand on the base of the chamber or rest on a rack. In a laundry washing machine it could move freely.

In a laundry washing machine the device may suitably be a sphere or ovoid, so as to move freely with the laundry without causing abrasion. In use, when in a dry phase, it is able to release the air treatment agent, which, given the proximity of the laundry, may in practice be regarded as a laundry treatment agent. Alternatively a device could be secured by a hole of the drum of the laundry washing device, using a hook.

A solid source of the air treatment agent may comprise an evaporable block, that is, a block which entirely evaporates, in use. Alternatively it could comprise a block into which an air treatment agent is adsorbed; the block is a carrier which is removed when the air treatment agent is exhausted. Such a block could contain a colour change agent to provide a visual indication of exhaustion of the air treatment agent.

If such a block is used in the present invention emanation of the air treatment agent into air can occur in dry phases of operation, but emanation of the air treatment agent by water, during wet phases, is inhibited.

A liquid air treatment agent may comprise a sac or blister, in which a concentrate liquid air treatment agent is retained within a membrane, through which the liquid treatment agent can diffuse. This is an arrangement which is employed in the arrangement of WO 2005/102141 A1. In WO 2005/102141 A1 the sac or blister conveys the air treatment agent by diffusion to the membrane surface, from which it evaporates into the air, or is conveyed away by water, during a wet phase.

If such a sac or blister is used in the present invention emanation of the air treatment agent can occur in dry phases of operation, but emanation of the air treatment agent by water during wet phases, is inhibited.

The source of the air treatment agent may be provided in a replaceable body, to be located in a designated location in the emanation device. The source of the air treatment agent may be provided with a removable cover, for example a peel-off foil, to be removed shortly before insertion into the emanator device.

The membrane suitably comprises a water-insoluble polymer. A suitable polymer comprises a polyetheresteramide having an ordered arrangement of ester and amide functions, wherein the alcohol component comprises a monomeric or oligomeric diol. However other polymers are suitable.

It is found, in the present invention, that using openings as described provides emanation of an active treatment agent into air, without compromise compared with earlier devices of the type described above; but is effective in inhibiting unwanted release of active treatment agent into liquid water, when the emanator device is wet.

In accordance with a second aspect of the present invention there is provided an air treatment method for use in a household apparatus which has dry phases of operation and wet phases of operation, wherein the method provides the emanation of an air treatment agent during the dry phases but not during the wet phases, wherein the method employs an emanator device, comprising a housing which contains a solid or liquid source of the air treatment agent, wherein the housing comprises a wall and a plurality of openings, wherein the openings are the only openings available for the emanation of the air treatment agent, wherein each of the openings is sufficiently small, that selectively during a wet phase it is closed by a film or plug of water.

The household apparatus may be a dishwashing machine, a laundry washing machine, and a lavatory.

Preferably the method is one in which, during the wet phases, the emanator device is subjected to water in a non-immersive manner. For example in a lavatory such an emanator device may be washed over by a turbulent water-air mixture, when the lavatory is flushed. In the case of a dishwashing machine the emanator device is subject to water sprayed from the spray arm within the machine. However even when the device is fully immersed it is expected that water occluding the openings will inhibit the flow of the air treatment agent, our of the emanator device.

Figure 2:
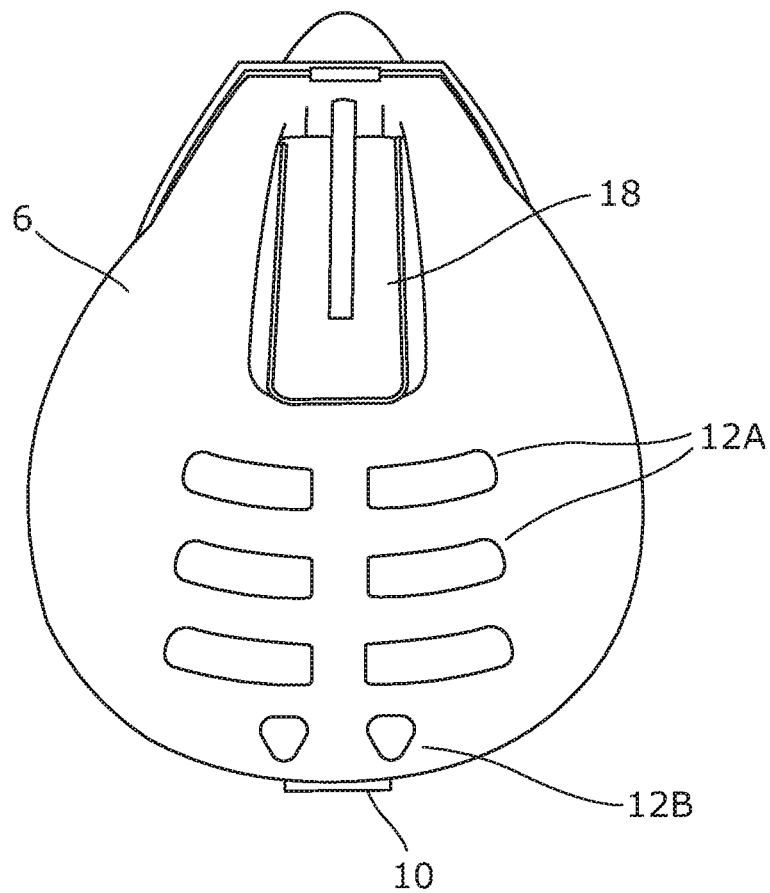
FIG. 2 shows the emanator device of FIG. 1 in rear elevation.
Figure 3:
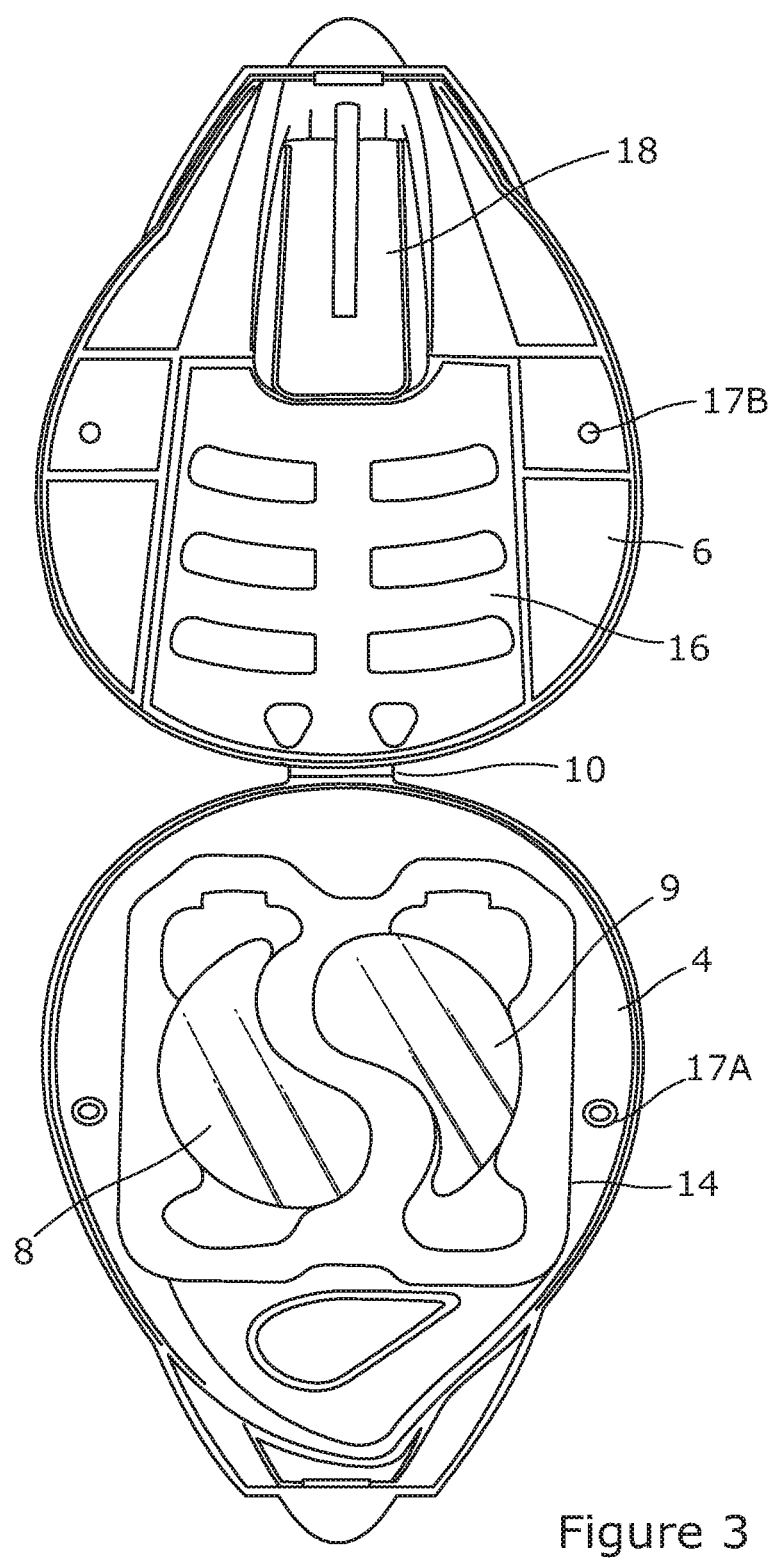
FIG. 3 shows the emanator device in elevation, with the device opened out to show its interior.
Figure 4:
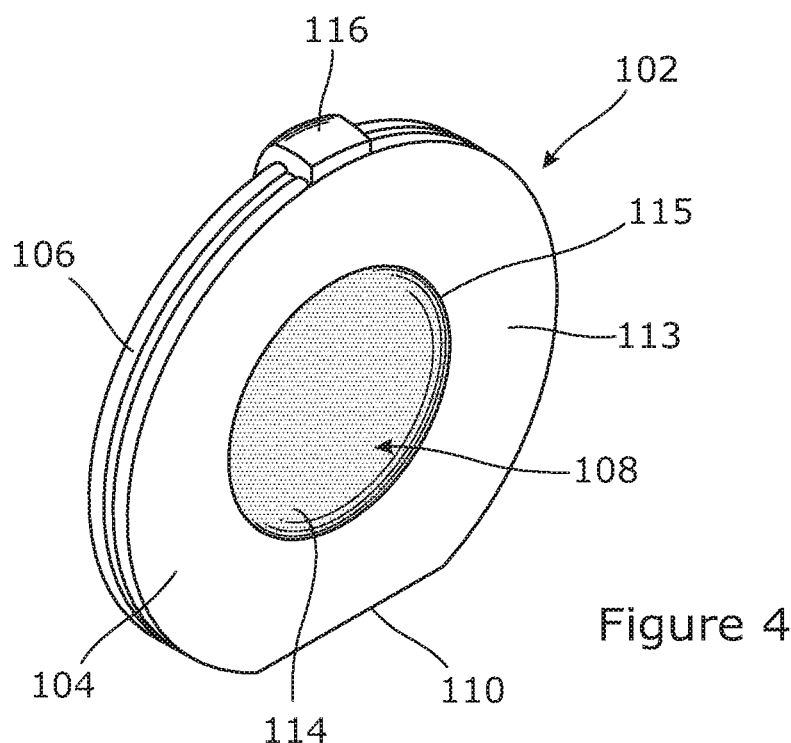
FIG. 4 shows a second embodiment of emanator device in a front perspective view.
Figure 5:
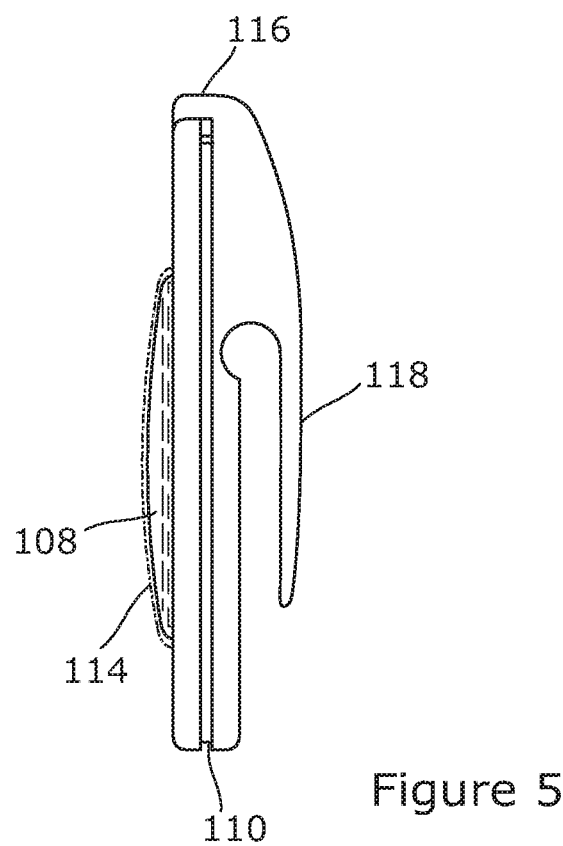
FIG. 5 shows the emanator device of FIG. 4 in side elevation.

An emanator device in accordance with the invention will now be described, by way of example, with reference to the following drawings, in which:

FIG. 1 shows a first embodiment of emanator device in front elevation;

FIG. 2 shows the emanator device of FIG. 1 in rear elevation;

FIG. 3 shows the emanator device in elevation, with the device opened out to show its interior;

FIG. 4 shows a second embodiment of emanator device in a front perspective view; and FIG. 5 shows the emanator device of FIG. 4 in side elevation.

The emanator device shown in FIGS. 1, 2 and 3 comprises a housing 2 formed of front and rear shell-halves or panels 4 and 6 and, retained between the shell-halves, two differently-coloured blisters 8, 9. The two shell-halves are joined together by a web hinge 10. The two shell-halves and the web hinge are formed as one moulding.

The front shell-half 4 has two openings through which the respective blisters can be seen. The openings are covered by a transparent "windows" of plastics material. However the "windows" are not transpirant. That is to say, a fragrance (or other air treatment agent) which emanates from the blisters cannot pass through these plastics "windows". In fact, they cannot pass through any part of the front shell-half 4.

The rear shell-half has eight apertures 12A, six larger apertures and two smaller peripheral apertures 12B. These are not closed by any plastics material, or other material which would prevent the flow of gases (e.g. air, fragrance) from the interior of the emanator device, to the surrounding environment.

FIG. 3 shows that the blisters are provided in a separable body 14, which is provided as a replacement unit, which can be inserted into a designated location in the front shell-half 4. A fine gauze 16 is retained within the rear shell-half. The gauze 16, a fine gauze of stainless steel, has openings which are approximately 0.2 mm×0.2 mm rectangles. When the shell-halves are closed together, and are retained by peg and hole connections 17A, 17B, to provide the configuration shown in FIGS. 1 and 2, the gauze overlies the blisters, in a sufficiently tight fit that fragrance leaving the blisters must flow through the gauze, in order to be emanated.

The rear shell-half has at its top side, remote from the web-hinge 10, a projecting hook 18, formed as part of its moulding. By means of the hook the emanator device may be secured to a horizontal bar within a dishwashing machine.

Each blister comprises a sac containing a fragrance. The wall of the sac is composed of a polyetheresteramide plastics material which permits diffusion or transpiration of the fragrance, from the interior of the sac to the outer surface of the sac. The objective is that the fragrance which diffuses to the outer surface of the sac then evaporates into the airspace within a dishwashing machine.

The emanator device, being a device for use in a dishwashing machine, inevitably experiences wet phases, and dry phases. Wet phases are active washing phases when wash water is present in the dishwashing machine. Dry phases include drying stages within a dishwashing cycle. Dry phases include the periods between one dishwashing operation and the next dishwashing operation. This includes periods when the user unloads the dishwashing machine; and the periods during which dirty articles are loaded into and stored in the dishwashing machine.

It is desirable that fragrance emanation takes place during dry phases. However it is undesirable for there to be emanation of fragrance during a wet phase, because the fragrance will enter the water and may lead to a detectable, undesired, taint.

The gauze 16 does not represent a barrier of any significance to airborne fragrance, during a dry phase of operation. However during a wet phase it does provide a barrier. The ambient water is adsorbed onto the gauze, as films or plugs of water (or as a consolidated film of water).

The emanator device shown in FIGS. 4 and 5 comprises a housing 102 formed of front and rear shell-halves 104, 106 and, retained between the shell halves, a blister 108. The blister comprises a sac containing a fragrance, and is replaceable. The two shell halves are joined together by a web hinge 110. The two shell halves and the web hinge are formed as one moulding.

The rear shell-half 106 has a wall which is without any apertures, and thus presents an absolute barrier to the release or air treatment agent from the emanator device. The front shell-half 104 has an annular wall 113 which also presents a barrier to the 10 passage of the air treatment agent, but which defines a large, central, circular aperture 115, which is aligned with the blister 108.

A fine gauze 114, of stainless steel, covers the aperture 115. The size of each opening of the gauze is approximately 0.2 mm×0.2 mm. The periphery of the gauze is located inside the emanator device, and by this means the gauze is retained securely in place. Where the gauze is in alignment with the blister (i.e. where the gauze can be seen, in FIGS. 4 and 5) the gauze is slightly domed, so that it is spaced from the blister. This can be seen in FIG. 5.

The rear shell-half has at its top side, remote from the web-hinge 110, a projecting clasp 116 which extends over the edge of the front shell-half, when the two shell-halves are brought together, to secure one to the other, with the blister trapped between them. The arrangement is such that the two shell-halves are joined together in such a way that water cannot enter the device between the two shell-halves; they seal against one another.

The rear shell-half also has a hook 118, formed as part of its moulding. By means of the hook 118, the emanator device may be secured to a horizontal bar within a dishwashing machine.

The wall of the sac is composed of a polyetheresteramide plastics material which permits diffusion of the fragrance, from the interior of the sac to the outer surface of the sac. The objective is that the fragrance which diffuses to the outer surface of the sac then evaporates into the air space within the dishwashing machine.

The operation of the second embodiment is the same as that of the first embodiment. The gauze causes the release profile of the air treatment agent to differ, between dry and wet phases of operation.

The operation of the device as described in the first embodiment of FIGS. 1 to 3, in achieving the objects described herein, was tested in laboratory experiments, which are described in Example Sets 1, 2 and 3 below.

EXAMPLES

The present invention is also described and demonstrated by way of the following examples. However, the use of these and other examples anywhere in the specification is illustrative only and in no way limits the scope and meaning of the invention or of any exemplified term Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Example Set 1

Two identical emanator devices as described above with reference to FIGS. 1 to 3, and containing lemon and lime fragrance (called A and B) were tested in comparison with two emanator devices (called C and D) which were identical to devices A and B, except for not having the gauze 14. The four devices were subjected to the same 10 runs (washes) in a Constructa PA 300 dishwashing machine, using a normal 65° C. programme. A standard Finish (Registered Trade Mark) dishwashing tablet was used for each wash, and Finish Rinse Aid. Thus, the laboratory conditions represented normal wash conditions, with a standard load comprising cutlery, ceramic plates, plastic bowls and glasses. The devices were weighed after each run. The results are presented in Tables 1 and 2 below.

TABLE 1

| | Remaining weight of blister and perfume (g) | | | |
|---|---|---|---|---|
| Wash operation | A (inv) | B (inv) | C (comp) | D (comp) |
| Start | 6.009 | 6.077 | 6.095 | 6.165 |
| Run 1 | 5.898 | 5.950 | 5.958 | 6.007 |
| Run 2 | 5.737 | 5.787 | 5.758 | 5.804 |
| Run 3 | 5.654 | 5.715 | 5.638 | 5.688 |
| Run 4 | 5.578 | 5.642 | 5.521 | 5.574 |
| Run 5 | 5.438 | 5.506 | 5.350 | 5.401 |
| Run 6 | 5.355 | 5.426 | 5.226 | 5.287 |
| Run 7 | 5.274 | 5.341 | 5.097 | 5.157 |
| Run 8 | 5.187 | 5.266 | 4.972 | 5.037 |
| Run 9 | 5.068 | 5.158 | 4.837 | 4.892 |
| Run 10 | 4.983 | 5.072 | 4.705 | 4.760 |

TABLE 2

| | Weight loss as % | | | |
|---|---|---|---|---|
| Wash operation | A (inv) | B (inv) | C (comp) | D (comp) |
| Start | 0.00 | 0.00 | 0.00 | 0.00 |
| Run 1 | 2.46 | 2.77 | 2.98 | 3.39 |
| Run 2 | 6.03 | 6.34 | 7.33 | 7.74 |
| Run 3 | 7.87 | 7.91 | 9.95 | 10.23 |
| Run 4 | 9.56 | 9.50 | 12.49 | 12.67 |
| Run 5 | 12.66 | 12.48 | 16.21 | 16.38 |
| Run 6 | 14.50 | 14.22 | 18.91 | 18.82 |

TABLE 2-continued

|  | Weight loss as % | | | |
| --- | --- | --- | --- | --- |
| Wash operation | A (inv) | B (inv) | C (comp) | D (comp) |
| Run 7 | 16.30 | 16.08 | 21.72 | 21.61 |
| Run 8 | 18.23 | 17.72 | 24.44 | 24.18 |
| Run 9 | 20.87 | 20.08 | 27.38 | 27.29 |
| Run 10 | 22.75 | 21.96 | 30.25 | 30.12 |

Example Set 2

In a further set of tests emanator devices E, F, G and H, which were replicates of devices A, B, C and D, were tested for weight loss under dry phase conditions in a drying open at 40° C. and at 75% relative humidity. The results are given below in Tables 3 and 4.

TABLE 3

|  | Remaining weight of emanator device | | | |
| --- | --- | --- | --- | --- |
| Time | E (inv) | F (inv) | G (comp) | H (comp) |
| Start | 17.296 | 18.014 | 13.247 | 13.288 |
| After 24 hours | 17.061 | 17.775 | 12.962 | 13.024 |
| After 48 hours | 16.853 | 17.570 | 12.723 | 12.794 |
| After 72 hours | 16.680 | 17.392 | 12.550 | 12.608 |
| After 6 days | 16.283 | 17.007 | 12.145 | 12.181 |
| After 14 days | 15.700 | 16.438 | 11.624 | 11.658 |
| After 1 month | 15.265 | 15.947 | 11.189 | 11.216 |

TABLE 4

|  | Weight loss as % | | | |
| --- | --- | --- | --- | --- |
| Time | E (inv) | F (inv) | G (comp) | H (comp) |
| Start | 0.00 | 0.00 | 0.00 | 0.00 |
| After 24 hours | 6.16 | 6.19 | 7.41 | 6.88 |
| After 48 hours | 11.62 | 11.51 | 13.63 | 12.87 |
| After 72 hours | 16.15 | 16.12 | 18.13 | 17.72 |
| After 6 days | 26.56 | 26.09 | 28.67 | 28.84 |
| After 14 days | 41.84 | 40.84 | 42.22 | 42.47 |
| After 1 month | 53.25 | 53.56 | 53.54 | 53.99 |

Example Set 3

In a further set of tests emanator devices I, J, K and L, being replicates of emanator device A, were tested in comparison with emanator devices M and N, which were replicates of emanator device C. The six devices were subjected to the same 60 runs (washes) in a Miele GSA4 dishwashing machine, using a normal 65° C. programme. A standard Finish (Registered Trade Mark) dishwashing tablet was used for each wash, and Finish Rinse Aid. Thus, the laboratory conditions represented normal wash conditions, with a standard load comprising cutlery, ceramic plates, plastic bowls and glasses. The devices were weighed after each run. The results are presented in Tables 5 and 6 below.

TABLE 5

|  | Remaining weight of blister and perfume (g) | | | | | |
| --- | --- | --- | --- | --- | --- | --- |
| Wash operation | I (inv) | J (inv) | K (inv) | L (inv) | M (comp) | N (comp) |
| Start | 16.219 | 16.433 | 16.482 | 16.352 | 15.291 | 15.311 |
| After 20 cycles | 15.277 | 15.464 | 15.496 | 15.378 | 13.940 | 14.038 |
| After 40 cycles | 14.537 | 14.724 | 14.639 | 14.572 | 12.741 | 12.517 |
| After 60 cycles | 13.854 | 13.980 | 13.917 | 13.808 | 11.640 | 11.837 |

Example Set 2 shows no difference in fragrance emanation into air, in a comparison under dry conditions, between an emanator device with the gauze, and the same emanator device without the gauze. Example Set 1 shows that there is a considerable difference in fragrance release, under the alternating wet/dry conditions of the dishwashing machine, between emanator devices with a gauze and emanator devices without the gauze. In the emanator devices without the gauze, the weight loss, over 10 machine washing operations, was substantially higher than the weight loss from the emanator devices having the gauze. Example Set 3 also showed large differences in weight losses, and a progressively increasing differential, over 20, 40 and 60 cycles, between emanator devices with a gauze, and without the gauze; the former showing considerably lower weight losses.

The results can be explained on the basis that in the emanator devices without the gauze water is free to come into contact with the blister, and thereby carry away perfume. This is inefficient (because this is not the intended use of the perfume) and undesirable (because of the resulting taint, which some users can detect); whereas when the gauze is present water is inhibited from coming into contact with the blister.

However under dry conditions, there is no such inhibition. Thus emanation takes place efficiently during dry phases and is inhibited during wet phases.

While several possible embodiments are disclosed above, embodiments of the present invention are not so limited. These exemplary embodiments are not intended to be exhaustive or to unnecessarily limit the scope of the invention, but instead were chosen and described in order to explain the principles of the present invention so that others skilled in the art may practice the invention. Indeed, various modifications of the invention in addition to those described herein will become apparent to those skilled in the art from the foregoing description. Such modifications are intended to fall within the scope of the appended claims. Further, the terminology employed herein is used for the purpose of describing exemplary embodiments only and the terminology is not intended to be limiting since the scope of the various embodiments of the present invention will be limited only by the appended claims and equivalents thereof. The scope of the invention is therefore indicated by the following claims, rather than the foregoing description and above-discussed embodiments, and all changes that come within the meaning and range of equivalents thereof are intended to be embraced therein.

Disclosed are methods and compositions that can be used for, can be used in conjunction with, can be used in preparation for, or are products of the disclosed methods and compositions.

These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

All patents, applications, publications, test methods, literature, and other materials cited herein are hereby incorporated by reference in their entirety as if physically present in this specification.

What is claimed is:

1. An emanator device for emanating an air treatment agent into the surrounding air of a dishwashing machine, the emanator device comprising a housing which contains a source of an air treatment agent,
    wherein the housing comprises a wall and a plurality of openings,
    wherein the openings are the only openings available for passage into the surrounding air of the dishwashing machine of the air treatment agent emanated by the source thereof, and
    wherein each of the openings is sufficiently small that each opening is configured to be closed by a film of water or plug of water when the emanator device is subjected to water in a non-immersive manner inside the dishwashing machine, and
    wherein the area of each opening does not exceed 0.5 mm$^2$, and
    wherein the housing is in a form selected from the group consisting of flat, discoid, spheroid, and ovoid, and comprises separable front and rear panels.

2. The emanator device as claimed in claim 1, wherein the total area of the openings is not less than 50 mm$^2$.

3. The emanator device as claimed in claim 1, wherein the openings are arranged as an array or group.

4. The emanator device as claimed in claim 3, wherein the openings are provided as a gauze.

5. The emanator device as claimed in claim 4, wherein said gauze is mounted in a window in the wall of the housing, and represents the only exit route from the device, for the treated air.

6. The emanator device as claimed in claim 1, wherein the air treatment agent comprises an agent selected from the group consisting of a fragrance, an airborne sanitizing agent, and an airborne malodor absorber.

7. The emanator device as claimed in claim 1, wherein the area of each opening does not exceed 0.1 mm$^2$.

8. The emanator device as claimed in claim 1, wherein the total area of the openings is not less than 100 mm$^2$.

* * * * *